United States Patent
Hyun et al.

(10) Patent No.: US 8,447,383 B2
(45) Date of Patent: May 21, 2013

(54) SYSTEM AND METHOD FOR PROVIDING 2-DIMENSIONAL COMPUTERIZED-TOMOGRAPHY IMAGE CORRESPONDING TO 2-DIMENSIONAL ULTRASOUND IMAGE

(75) Inventors: Dong Gyu Hyun, Seoul (KR); Jong Beom Ra, Daejeon (KR); Duhgoon Lee, Daejeon (KR); Woo Hyun Nam, Busan (KR)

(73) Assignees: Medison Co., Ltd., Kangwon-do (KR); Korea Advanced Institute of Science and Technology, Daejeon (KR)

( * ) Notice: Subject to any disclaimer, the term of this patent is extended or adjusted under 35 U.S.C. 154(b) by 197 days.

(21) Appl. No.: 12/848,024

(22) Filed: Jul. 30, 2010

(65) Prior Publication Data

US 2011/0028844 A1     Feb. 3, 2011

(30) Foreign Application Priority Data

Aug. 3, 2009 (KR) ................. 10-2009-0071351

(51) Int. Cl.
*A61B 5/05* (2006.01)
(52) U.S. Cl.
USPC ........................................................ 600/427
(58) Field of Classification Search
None
See application file for complete search history.

(56) References Cited

U.S. PATENT DOCUMENTS

| | | | |
|---|---|---|---|
| 5,640,956 | A | 6/1997 | Getzinger et al. |
| 2008/0137927 | A1 | 6/2008 | Altmann et al. |
| 2009/0093717 | A1 | 4/2009 | Carneiro et al. |

FOREIGN PATENT DOCUMENTS

| | | |
|---|---|---|
| JP | 2008-086400 A | 4/2008 |
| JP | 2009-291618 | 12/2009 |
| KR | 10-2008-0053057 A | 6/2008 |
| KR | 10-2008-0053224 A | 6/2008 |

OTHER PUBLICATIONS

Huang et al. "Dynamic 2D Ultrasound and 3D CT Image Registration of the Beating Heart," IEEE Transactions on Medical Imaging, vol. 28, No. 8, pp. 1179-1189, 2009.*

Nam et al. "Anatomical feature extraction in 3D B-mode ultrasound liver images for CT-ultrasound image registration," Int J CARS, vol. 3 (Suppl 1), pp. S401-S402, 2008.*

Porter et al. "Three Dimensional Frameless Fusion of Ultrasound Liver Volumes," 1999 IEEE Ultrasonics Symposium, pp. 1577-1580.*

Huang et al., "Dynamic 2D Ultrasound and 3D CT Image Registration of the Beating Heart," IEEE Transactions on Medical Imaging, 28(8):1179-1189 (Aug. 2009).

(Continued)

*Primary Examiner* — Long V. Le
*Assistant Examiner* — Faizah Ahmed
(74) *Attorney, Agent, or Firm* — McDermott Will & Emery LLP (57) ABSTRACT

Embodiments for providing a 2-dimensional (D) computerized-tomography (CT) image corresponding to a 2-D ultrasound image through image registration between 3-D ultrasound and CT images are disclosed. An imaging system comprises a CT imaging unit, an ultrasound image forming unit, a storing unit, a processor and a display unit. The processor extracts the 2-D CT image from the 3-D ultrasound-CT registered image by performing a rigid-body transform upon the 3-D ultrasound image and calculating similarities between reference images and the 2-D ultrasound images, wherein the reference images are obtained through the rigid-body transform.

10 Claims, 5 Drawing Sheets

OTHER PUBLICATIONS

Lee et al., "Sensorless and Real-Time Registration Between 2D Ultrasound and Preoperative Images of the Liver," IEEE 978-1-4244-4126-6/10, XP-002602573, pp. 388-391 (2010).

Nam et al., "Anatomical Feature Extraction in 3D B-Mode Ultrasound Liver Images for CT-Ultrasound Image Registration," Int. J. CARS, 3 (Suppl. 1):S330-417, XP-002602575 (2008).

Extended European Search Report for EP 10170225-6-2218, 6 pages, mailed Oct. 26, 2010.

Korean Notice of Allowance issued in Korean Patent Application No. 10-2009-0071351, dated Feb. 3, 2012.

Bortfeld et al., *Effects of intra-fraction motion on IMRT dose delivery: statistical analysis and simulation*, Phys. Med. Biol. 47, pp. 2203-2220 (2002).

Korean Office Action issued in Korean Patent Application No. 10-2009-0071351, dated Sep. 27, 2011.

Pitiot et al., "Piecewise Affine Registration of Biological Images for Volume Reconstruction," Medical Image Analysis, Elsevier, 19 pages (Received Aug. 9, 2004).

\* cited by examiner

$|\lambda_1|$ : Very low
$|\lambda_2|$ : Very low
$|\lambda_3|$ : High

SYSTEM AND METHOD FOR PROVIDING 2-DIMENSIONAL COMPUTERIZED-TOMOGRAPHY IMAGE CORRESPONDING TO 2-DIMENSIONAL ULTRASOUND IMAGE

CROSS-REFERENCE TO RELATED APPLICATIONS

The present application claims priority from Korean Patent Application No. 10-2009-0071351, filed on Aug. 3, 2009, the entire subject matter of which is incorporated herein by reference.

TECHNICAL FIELD

The present disclosure generally relates to ultrasound imaging, and more particularly to a system and method for providing a 2-dimensional (D) computerized-tomography (CT) image corresponding to a 2-D ultrasound image through image registration between 3-D ultrasound and CT images of a target object.

BACKGROUND

An ultrasound diagnostic system has been extensively used in the medical field due to its non-invasive and non-destructive nature. The ultrasound diagnostic system can provide an ultrasound image of the inside of a target object in real-time without resorting to any incisions. However, the ultrasound diagnostic system suffers from inherent shortcomings of an ultrasound image such as a low signal-to-noise ratio and a limited field of view. Thus, an image registration between a CT image and an ultrasound image has been introduced to compensate for inherent deficiencies of the ultrasound image.

Generally, an image registration between a CT image and an ultrasound image is performed by means of a spatial sensor. Errors may occur during the image registration due to spatial movement variation in the inner part of a target object such as respiration. If an ultrasound probe is moved and a 2-D ultrasound image is newly obtained, then the spatial sensor is typically used to determine whether or not the newly obtained 2-D ultrasound image exists in a pre-obtained 3-D ultrasound image, and to extract a 2-D CT image corresponding to the newly obtained 2-D ultrasound image from a 3-D ultrasound-CT registered image.

SUMMARY

There are disclosed embodiments for providing a 2-D CT image corresponding to a 2-D ultrasound image through an image registration between 3-D ultrasound and CT images of a target object, independent of a spatial sensor. In an exemplary embodiment, by way of non-limiting example, an image system comprises: a computerized-tomography (CT) imaging unit configured to form a 3-dimensional (D) CT image of a target object; an ultrasound image forming unit configured to form 3- and 2-D ultrasound images of the target object; a storing unit configured to store sets of transform parameters for use in performing a rigid-body transform upon the 3-D ultrasound image; a processor configured to perform an image registration between the 3-D ultrasound and CT images, establish a 3-D coordinate system with a reference surface being set thereon in the 3-D ultrasound image, perform the rigid-body transform upon the 3-D ultrasound image by sequentially applying the sets of transformation parameters retrieved from the storing unit, calculate similarities between reference images corresponding to the reference surface and the 2-D ultrasound image, and extract a 2-D CT image corresponding to the 2-D ultrasound image from the 3-D ultrasound-CT registered image based on the calculated similarities; and a display unit configured to display the 2-D ultrasound image and the resultant 2-D CT image, wherein each of the reference images is obtained at every rigid-body transform when the sets of transformation parameters are sequentially applied thereto and the 2-D ultrasound image is related to a region of interest (ROI) of the target object.

In another embodiment, a method of imaging comprises: forming 3-D ultrasound and CT images of a target object; performing an image registration between the 3-D ultrasound and CT images to form a 3-D ultrasound-CT registered image; forming a 2-D ultrasound image related to a region of interest (ROI) of the target object; establishing a 3-D coordinate system with a reference surface being set thereon in the 3-D ultrasound image; performing a rigid-body transform upon the 3-D ultrasound image by sequentially applying sets of transform parameters and calculating similarities between reference surface images and the 2-D ultrasound image, wherein each of the reference surface images is obtained every rigid-body transform when the sets of transform parameters are sequentially applied thereto and each of the reference surface images corresponds to the reference surface; extracting a 2-D CT image corresponding to the 2-D ultrasound image from the 3-D ultrasound-CT registered image based on the calculated similarities; and displaying the 2-D ultrasound and CT images.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
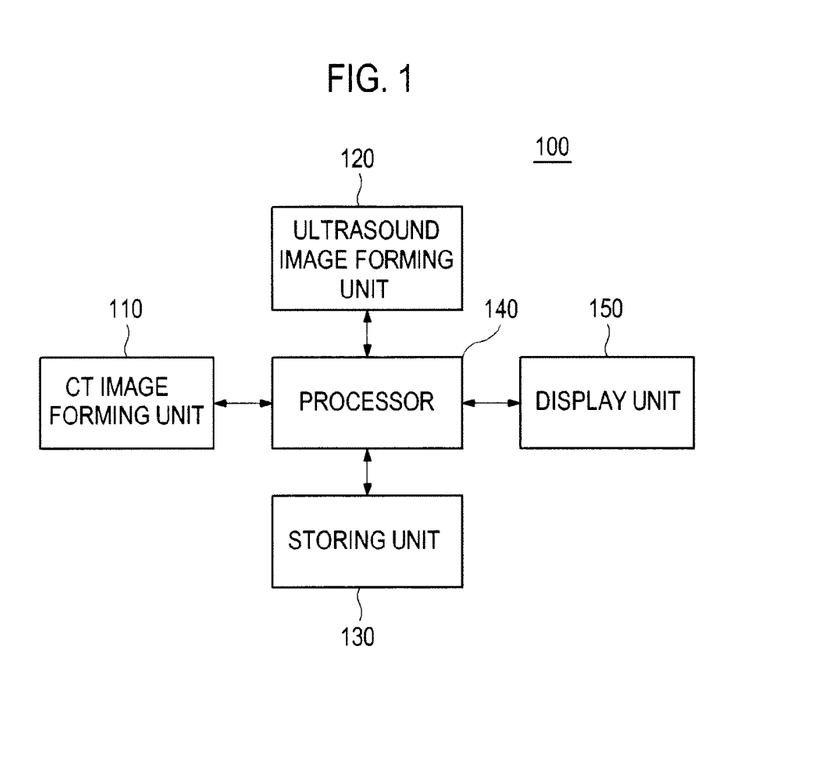
FIG. 1 is an embodiment illustrating a schematic diagram of an ultrasound imaging system in accordance with the present disclosure.

Referring to FIG. 1, there is shown an embodiment illustrating a schematic diagram of an ultrasound imaging system 100 in accordance with the present disclosure. In an exemplary embodiment, the ultrasound imaging system 100 may comprise a computerized-tomography (CT) image forming unit 110, an ultrasound image forming unit 120, a storing unit 130, a processor 140 and a display unit 150. The ultrasound imaging system 100 may further comprise a user input unit (not shown) configured to receive input data from a user.

The CT image forming unit 110 may be configured to form a 3-D CT image of a target object (e.g., a liver). It is noted that the formation of the 3-D CT image may be accomplished by using techniques well known in the art. The 3-D CT image may be comprised of a plurality of 2-D CT images of the target object. The 3-D CT image of the target object is then sent to the processor 140.

The ultrasound image forming unit 120 may be configured to form 3- and 2-D ultrasound images of the target object. In particular, the ultrasound image forming unit 120 may be operable to transmit ultrasound signals to the target object and receive reflected ultrasound signals (i.e., ultrasound echo signals) therefrom to form the 3-D ultrasound image of the target object. Also, the ultrasound image forming unit 120 may be operable to transmit ultrasound signals to the target object and receive reflected ultrasound echo signals therefrom to form the 2-D ultrasound image with respect to a region of interest (ROI) of the target object.

Figure 2:
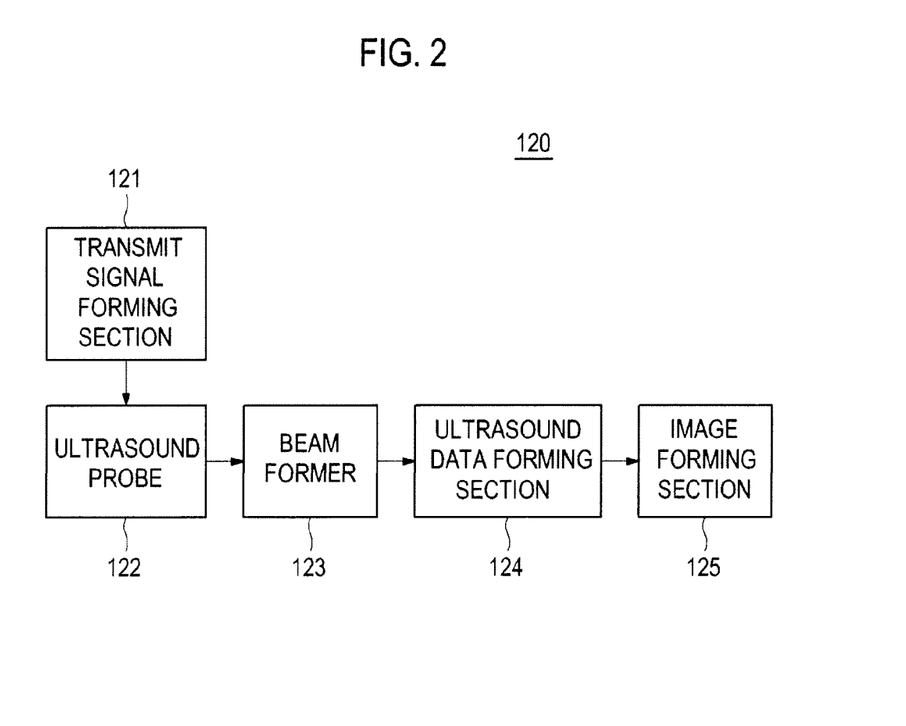
FIG. 2 is an embodiment illustrating a schematic diagram of an ultrasound image forming unit in accordance with the present disclosure.

Referring to FIG. 2, there is shown an embodiment illustrating a schematic diagram of the ultrasound image forming unit 120 in accordance with the present disclosure. In an exemplary embodiment, the ultrasound image forming unit 120 may include a transmit signal forming section 121, an ultrasound probe 122 having a multiplicity of transducer elements (not shown), a beam former 123, an ultrasound data forming section 124 and an image forming section 125.

The transmit signal forming section 121 may be configured to form first electrical transmit signals to obtain a plurality of image frames for use in imaging the 3-D ultrasound image in consideration of positions and focusing points of the transducer elements in the ultrasound probe 122. Also, the transmit signal forming section 121 may be configured to form second electrical transmit signals to obtain an image frame for use in imaging the 2-D ultrasound image in consideration of the positions and focusing points of the transducer elements. For example, the image frame may include a brightness (B)-mode image. Herein, the first and second electrical transmit signals may be selectively formed in response to input data from a user. The first and second electrical transmit signals are transmitted to the ultrasound probe 122.

In response to the first electrical transmit signals from the transmit signal forming section 121, the ultrasound probe 122 may be configured to generate and transmit ultrasound signals to the target object and then receive ultrasound echo signals reflected therefrom to form first electrical receive signals. Also, in response to the second electrical transmit signals from the transmit signal forming section 121, the ultrasound probe 122 may be configured to generate and transmit ultrasound signals to the target object and then receive ultrasound echo signals reflected therefrom to form second electrical receive signals. The first and second electrical receive signals are sent to the beam former 123.

The beam former 123 may be configured to receive the first electrical receive signals from the ultrasound probe 122 and convert them from analog to digital to form first digital signals. Thereafter, the beam former 123 may be operable to receive-focus the first digital signals in consideration of the positions and focusing points of the transducer elements to thereby form first receive-focus signals. Also, the beam former 123 may be configured to receive the second electrical receive signals from the ultrasound probe 122 and convert them from analog to digital to form second digital signals. Then, the beam former 123 may be operable to receive-focus the second digital signals in consideration of the positions and focusing points of the transducer elements to thereby form second receive-focus signals. The first and second receive-focus signals are sent to the ultrasound data forming section 124.

The ultrasound data forming section 124 may be configured to receive the first receive-focus signals from the beam former 123 and form first ultrasound data based on the first receive-focus signals received. Also, the ultrasound data forming section 124 may be configured to receive the second receive-focus signals from the beam former 123 and form second ultrasound data based on the second receive-focus signals received. In an exemplary embodiment, the ultrasound data forming section 124 may be configured to perform various signal processes (e.g., a gain adjustment, filtering and so on) upon the first and second receive-focus signals in order to form the first and second ultrasound data. The first and second ultrasound data are sent to the image forming section 125.

The image forming section 125 may be configured to receive the first ultrasound data from the ultrasound data forming section 124 and form a 3-D ultrasound image of the target object based on the received first ultrasound data. Also, the image forming section 125 may be configured to receive the second ultrasound data from the ultrasound data forming section 124 and form a 2-D ultrasound image with respect to the ROI of the target object based on the received second ultrasound data. The 3-D and 2-D ultrasound images are sent to the processor 140.

Referring back to FIG. 1, the storing unit 130 may be configured to store transform parameters for use in translating and rotating the 3-D ultrasound image of the target object. In an exemplary embodiment, the storing unit 130 may be operable to store sets of transform parameters (as shown below in Table 1, but not limited thereto) for performing a rigid-body transform upon the 3-D ultrasound image of the target object. Herein, x, y and z may represent width, height and depth axes, respectively, at the 3-D ultrasound image. Further, $\theta_x$, $\theta_y$ and $\theta_z$ may denote rotation components centering on the respective width, height and depth axes.

TABLE 1

Sets of Transform Parameters
(x, y, z, $\theta_x$, $\theta_y$, $\theta_z$)

$x_0, y_0, z_0, \theta_{x0}, \theta_{y0}, \theta_{z0}$
$x_1, y_0, z_0, \theta_{x0}, \theta_{y0}, \theta_{z0}$
$x_2, y_0, z_0, \theta_{x0}, \theta_{y0}, \theta_{z0}$
. . .
$x_n, y_0, z_0, \theta_{x0}, \theta_{y0}, \theta_{z0}$
$x_0, y_1, z_0, \theta_{x0}, \theta_{y0}, \theta_{z0}$
$x_0, y_2, z_0, \theta_{x0}, \theta_{y0}, \theta_{z0}$
. . .
$x_0, y_n, z_0, \theta_{x0}, \theta_{y0}, \theta_{z0}$
$x_0, y_0, z_1, \theta_{x0}, \theta_{y0}, \theta_{z0}$
$x_0, y_0, z_2, \theta_{x0}, \theta_{y0}, \theta_{z0}$
. . .
$x_0, y_0, z_n, \theta_{x0}, \theta_{y0}, \theta_{z0}$
$x_0, y_0, z_0, \theta_{x0}, \theta_{y1}, \theta_{z0}$
$x_0, y_0, z_0, \theta_{x0}, \theta_{y2}, \theta_{z0}$
. . .

TABLE 1-continued

Sets of Transform Parameters
$(x, y, z, \theta_x, \theta_y, \theta_z)$ $x_0, y_0, z_0, \theta_{x0}, \theta_{yn}, \theta_{z0}$
$x_0, y_0, z_0, \theta_{x0}, \theta_{y0}, \theta_{z1}$
$x_0, y_0, z_0, \theta_{x0}, \theta_{y0}, \theta_{z2}$
...
$x_0, y_0, z_0, \theta_{x0}, \theta_{y0}, \theta_{zn}$
...
$x_n, y_n, z_n, \theta_{xn}, \theta_{yn}, \theta_{zn}$ The processor 140 may be configured to carry out image registration between the 3-D CT image from the CT image forming unit 110 and the 3-D ultrasound image from the ultrasound image forming unit 120 to thereby form a 3-D ultrasound-CT registered image. The processor 140 may be further configured to extract a 2-D CT image corresponding to the 2-D ultrasound image from the 3-D ultrasound-CT registered image.

Figure 3:
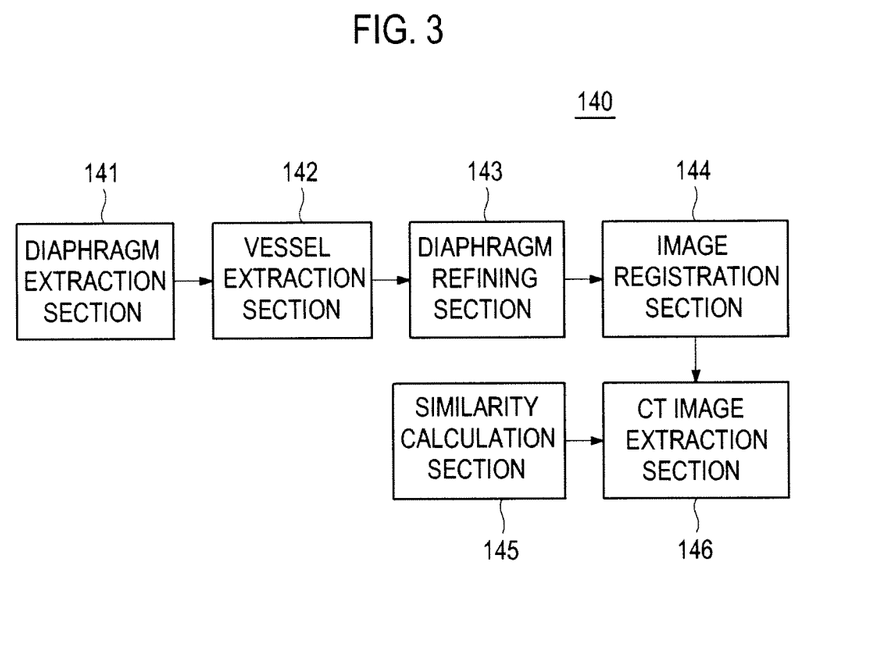
FIG. 3 is an embodiment illustrating a schematic diagram of a processor in accordance with the present disclosure.

As depicted in FIG. 3, there is shown an embodiment illustrating a schematic diagram of the processor 140 in accordance with the present disclosure. In an exemplary embodiment, the processor 140 may be configured to include a diaphragm extraction section 141, a vessel extraction section 142, a diaphragm refining section 143, an image registration section 144, a similarity calculation section 145 and a CT image extraction section 146.

The diaphragm extraction section 141 may be configured to extract a diaphragm from the 3-D ultrasound image received from the ultrasound image forming unit 120. Also, the diaphragm extraction section 141 may be configured to extract the diaphragm from the 3-D CT image received from the CT image forming unit 110. In an exemplary embodiment, the diaphragm extraction section 141 may be operable to perform a Hessian matrix based flatness test upon the respective 3-dimensional ultrasound and CT images to extract the diaphragm. The diaphragm may be considered as a curved surface in the respective 3-D ultrasound and CT images. Thus, regions, in which a voxel intensity change in a normal direction at a surface is greater than a voxel intensity change in a horizontal direction at the surface, may be extracted as the diaphragm.

In particular, the diaphragm extraction section 141 may select voxels having a relatively higher flatness than a reference flatness in order to extract the diaphragm. The voxels may be represented with pixels and the flatness $\mu(v)$ may be defined as the following equation (1).

$$\mu(v) = \phi_1(v)\phi_2(v)\phi_3(v)/\phi_{3_{max}}(v) \quad (1)$$

Figure 4:
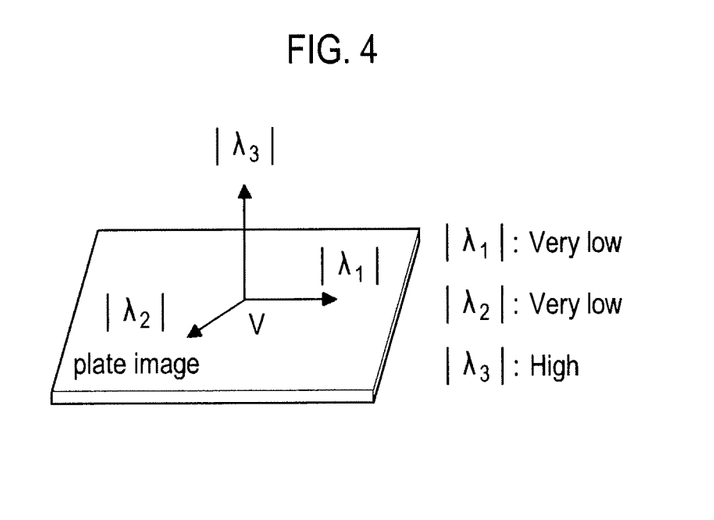
FIG. 4 is a schematic diagram illustrating an example of eigenvalues in the Hessian matrix.

$\phi_1(v)$, $\phi_2(v)$ and $\phi_3(v)$ in the equation (1) may be represented as the following equation (2).

$$\phi_1(v) = \left(1 - \frac{\lambda_1(v)}{\lambda_3(v)}\right)^2, \phi_2(v) = \left(1 - \frac{\lambda_2(v)}{\lambda_3(v)}\right)^2, \phi_3(v) = \sum_i \lambda_1(v)^2 \quad (2)$$

wherein $\lambda_1$, $\lambda_2$, and $\lambda_3$ denote eigenvalues of the Hessian matrix at voxel v. An example of the eigenvalues $\lambda_1$, $\lambda_2$, and $\lambda_3$ is illustrated in FIG. 4. The flatness $\mu(v)$ may be normalized to have values ranging from 0 to 1. A flatness map may be created based on the flatness obtained from all of the voxels according to the equations (1) and (2). Thereafter, the voxels having a relatively high flatness are selected. In an exemplary embodiment, the diaphragm extraction section 141 may be operable to select the voxels having the flatness over 0.1.

The diaphragm extraction section 141 may further perform morphological opening (i.e., morphological filtering) upon the selected voxels to remove small clutters therefrom. The morphological opening may be carried out by sequentially performing erosion and dilation. In particular, morphological boundaries in which the voxel values exist are removed as many as a predetermined number of the voxels and then contracted (erosion). Thereafter, the morphological boundaries are expanded as many as the predetermined number of the voxels. In an exemplary embodiment, the diaphragm extraction section 141 may contract and expand the morphological boundaries by 1 voxel.

The diaphragm is the largest surface in the respective 3-D ultrasound and CT images. The largest surface may be selected among candidates surfaces obtained by intensity-based connected component analysis (CCA) for the voxels and the selected surface may be regarded as the diaphragm. Voxel-based CCA is one of the methods of grouping regions in which voxel values exist. For example, it may be possible to compute the number of voxels connected to each of the voxels through a connectivity test by referring to values of voxels neighboring to the corresponding voxel (e.g., 26 voxels). The voxels, of which connected voxels are greater than the predetermined number, are selected as candidate groups. Since the diaphragm is the widest curved surface in the ROI of the respective 3-D ultrasound and CT images, the candidate group having the most connected voxels may be selected as the diaphragm. Thereafter, the surface of the diaphragm may be smoothened.

In another exemplary embodiment, while extracting the diaphragm from the 3-dimensional ultrasound image as described above, the diaphragm extraction section 141 may be operable to extract the diaphragm from the 3-D CT image, in response to input data from the user input unit (not shown), by using a commercial program or an extraction method, e.g., a seeded region growing segmentation method. The input data may include data for establishing a region of the diaphragm on the 3-D CT image and extracting the region therefrom.

The vessel extraction section 142 may be configured to perform vessel extraction upon the 3-D ultrasound and CT images sequentially through ROI masking, vessel segmentation and classification. In an exemplary embodiment, to avoid mis-extraction of vessels due to mirroring artifacts, the vessel extraction section 142 may be operable to perform the ROI masking upon the 3-D ultrasound and CT images by modeling the diaphragm to a polynomial curved surface. In such a case, the ROI masking, which models the diaphragm to the polynomial curved surface by using the least means square, may be used.

However, in case all of the lower portions of the modeled polynomial curved surface are eliminated, effective vessel information may be lost at some portion due to an error of the polynomial curved surface. In order to avoid losing the effective vessel information, the lower portion of the modeled polynomial curved surface may be eliminated in a marginal distance. For example, the marginal distance may be set to about 10 voxels at the lower portion of the ROI mask.

Subsequently, the vessel extraction section 142 may be further operable to segment a vessel region and a non-vessel region. In order to exclude non-vessel high intensity regions such as the diaphragm and vessel walls, the vessel extraction section 142 may estimate a low intensity boundary having a less reference boundary value in the ROI masked image. Thereafter, the vessel extraction section 142 may remove voxels with a higher intensity value than the reference boundary value. In an exemplary embodiment, an adaptive threshold scheme may be applied to the remaining regions for binarization thereof. The binarized segments may be labeled as vessel candidates.

Next, the vessel extraction section 142 may be further operable to remove non-vessel-type clutters from the binarization image to classify real vessels from the vessel candidates. In an exemplary embodiment, the vessel classification may include a size test for filtering out tiny background clutters, a structure-based vessel test, which evaluates the quality of fit to a cylindrical tube, for removing non-vessel type clutters (i.e., an initial vessel test), gradient magnitude analysis, and a final vessel test for perfectly removing the clutters from the binarization image. Although some clutters are not perfectly removed through the structure-based vessel test, an initial threshold may be marginally set so that all vessels may be included. For example, the initial threshold may be set to 0.6. At the final vessel test, clutters, which may be formed by small shading artifacts having low gradient magnitudes, may be perfectly removed in consideration with the variation of voxel values, i.e., gradient magnitudes, to thereby extract vessel data. In an exemplary embodiment, a threshold of the final vessel test may be set to 0.4.

In another exemplary embodiment, while extracting the vessel from the 3-dimensional ultrasound image as described above, the vessel extraction section 142 may be further operable to perform the vessel extraction upon the 3-D CT image, in response to input data from the user input unit. The input data may include data for establishing a region of the vessel on the 3-D CT image. In particular, the vessel extraction section 142 may set pixels having pixel values between a first threshold (T1) and a second threshold (T2) to have a value of 255 and the remaining pixels to have zero, by using pixel characteristics that the region of the vessel has a higher intensity than the remaining regions in the 3-D CT image. This process may be referred to as an intensity thresholding using two thresholds. As a result of such process, other regions having pixel values with higher intensities representing ribs and kidneys may be displayed as well as the vessel, i.e., the ROI. In order to eliminate the other regions rather than the vessel, connectivity of the vessel may be employed. In general, the vessel in a liver is comprised of a portal vein and a hepatic vein. The vessel extraction section 142 may be operable to establish two specific points corresponding to the portal vein and the hepatic vein as seed points and perform the seed region growing method using the seed points as starting points to thereby extract the vessel.

The diaphragm refining section 143 may be configured to perform refinement upon the diaphragm extracted in the 3-D ultrasound image by using the resultant vessel extracted from the vessel extraction section 142. In particular, the diaphragm refining section 142 may be operable to refine the diaphragm extracted from the 3-D ultrasound image by eliminating clutters by means of the resultant vessel. The clutters on the diaphragm extracted may be mainly placed near or on vessel walls. Especially, the vessel wall of an inferior vena cava (IVC) is likely to be connected to the diaphragm and cause clutters. These clutters may degrade the accuracy of feature based image registration so that the diaphragm should be refined. To refine the diaphragm, the vessel region is extracted according to the vessel extraction as described above, the extracted vessel region may be dilated, and then the dilated vessel region may be subtracted from the initially extracted diaphragm region to estimate vessel walls. The estimated vessel walls may be removed from the diaphragm region by performing the CCA and the size test once again.

The image registration section 144 may be configured to perform image registration between the 3-D ultrasound and CT images. The image registration section 144 may be operable to extract sample points corresponding to the vessel region and the diaphragm region, respectively, among the features extracted from the respective 3-D ultrasound and CT images In an exemplary embodiment, iterative closest point (ICP) based image registration may be performed with the sample points extracted from the respective 3-D ultrasound and CT images to thereby form a 3-D ultrasound-CT registered image.

The similarity calculation section 145 may be configured to calculate the similarity between the 2-D and 3-D ultrasound images while performing the rigid-body transform upon the 3-D ultrasound image. The operation of the similarity calculation section 145 will be described in detail hereinafter with reference to FIG. 5. The CT image extraction section 146 may be configured to extract a 2-D CT image corresponding to the 2-D ultrasound image from the 3-D ultrasound-CT registered image by means of the calculated similarity from the similarity calculation section 145.

Referring back to FIG. 1, the display unit 150 may be configured to display the 2-D ultrasound image related to the ROI and the 2-D CT image corresponding thereto. For example, the 2-D ultrasound image and the 2-D CT image may be superimposed over one another on the display unit 150. Alternatively, the 2-D ultrasound image and the 2-D CT image may be displayed on the display unit 150 in transverse or horizontal direction.

Hereinafter, operations for providing the 2-D CT image corresponding to the 2-dimensional ultrasound image from the 3-D ultrasound-CT registered image in accordance with an exemplary embodiment of the present disclosure will be described in detail with reference to FIGS. 5 to 7.

Figure 5:
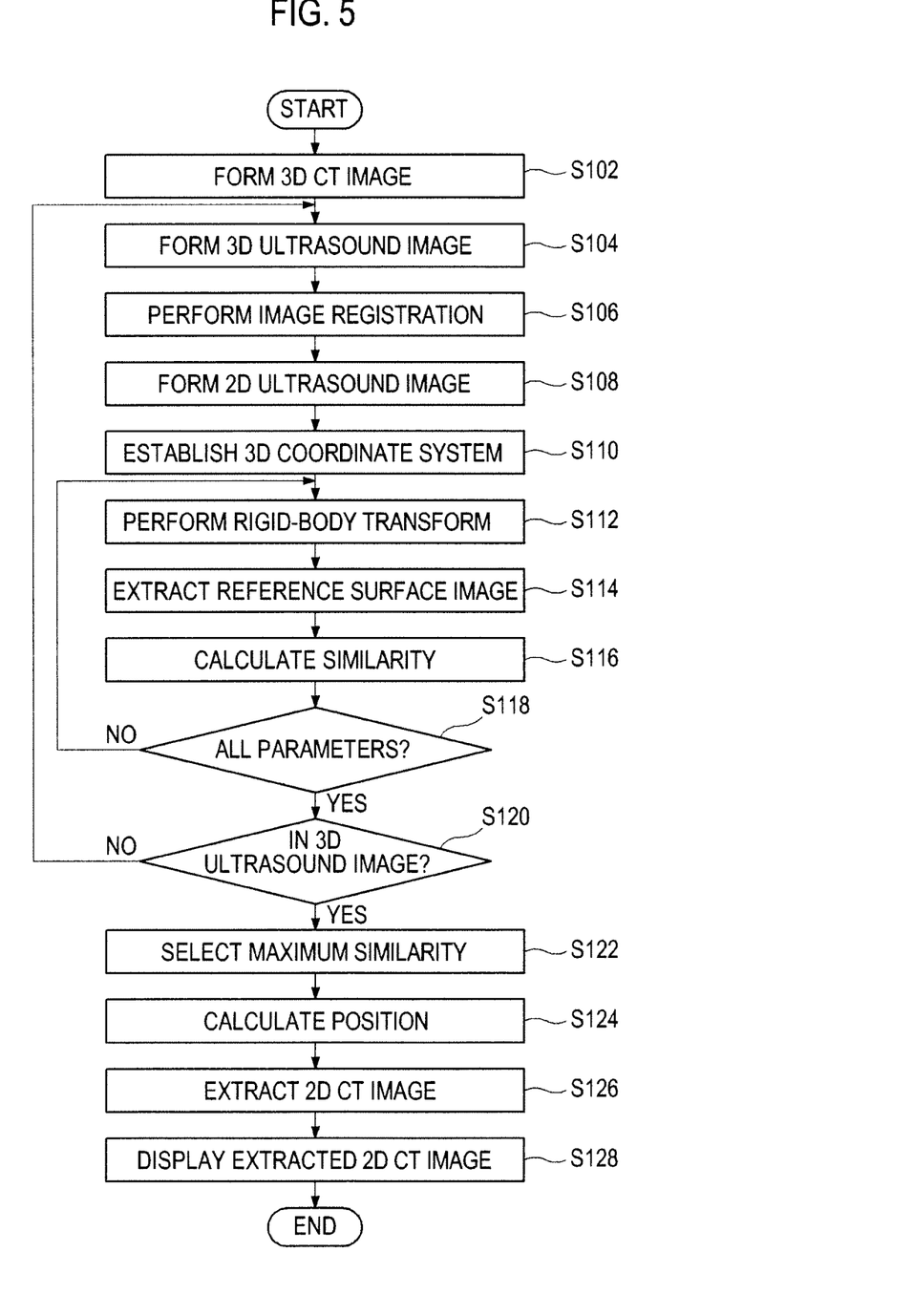
FIG. 5 is an embodiment illustrating a flowchart of a procedure for extracting a 2-D CT image corresponding to a 2-D ultrasound image from a 3-D ultrasound-CT registered image in accordance with the present disclosure.

Referring firstly to FIG. 5, the CT image forming unit 110 may be operable to form the 3-D CT image of the target object, at S102. The ultrasound image forming unit 120 may be operable to transmit ultrasound signals to the target object and receive ultrasound echo signals reflected therefrom to thereby form the 3-D ultrasound image of the target object, at S104.

The processor 140 may be operable to carry out image registration between the 3-D CT image from the CT image forming unit 110 and the 3-D ultrasound image from the ultrasound image forming unit 120 to thereby calculate a relative position of the 3-D ultrasound image with respect to the 3-D CT image, at S106.

Figure 6:
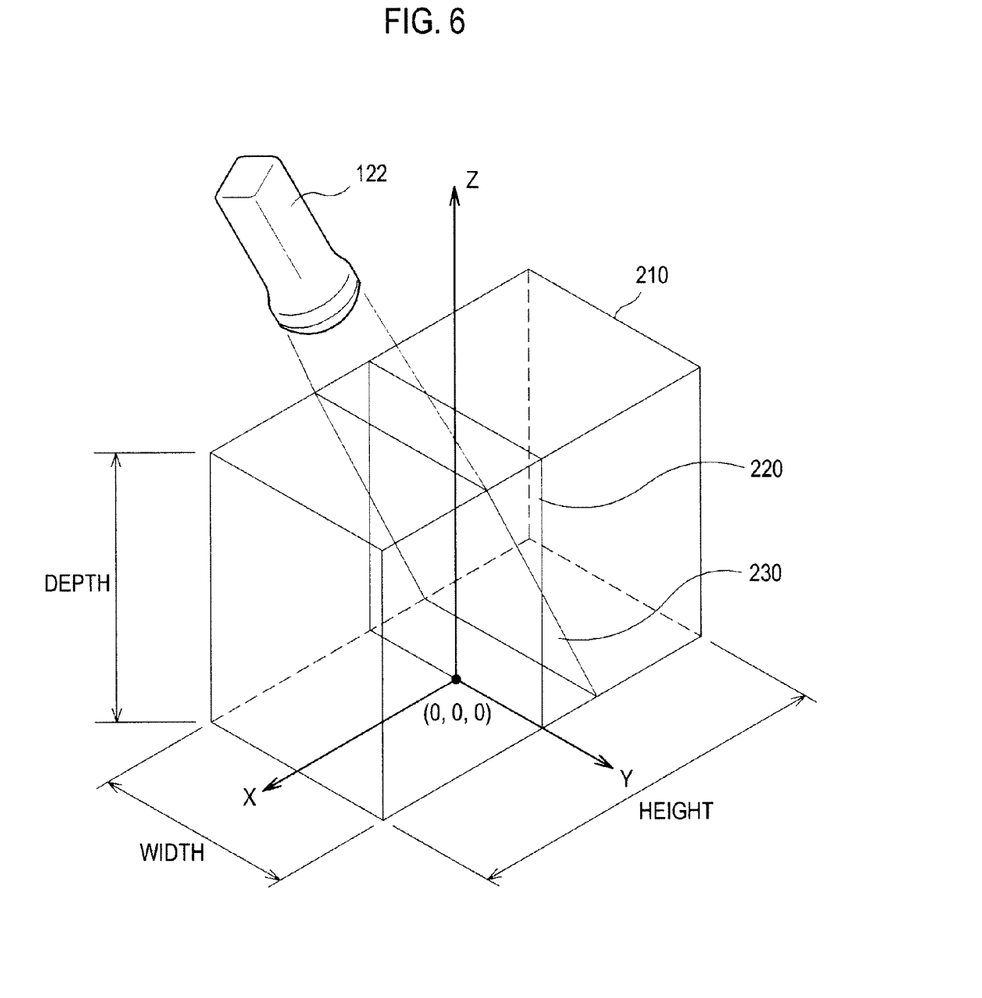
FIG. 6 is a schematic diagram illustrating examples of a 3-D ultrasound image, a 2-D ultrasound image, a 3-D coordinate system and a reference surface in accordance with the present disclosure.

The ultrasound image forming unit 120 may be operable to transmit ultrasound signals to the target object and receive ultrasound echo signals reflected therefrom to thereby form the 2-D ultrasound image 230 shown in FIG. 6 related to the ROI of the target object, at S108.

The similarity calculation section 145 of the processor 140 may be operable to establish the 3-D coordinate system with a reference surface 220 being set thereon in a 3-dimensional ultrasound image 210 as shown in FIG. 6, at S110. As depicted in FIG. 6, the reference surface 220 represents a cross-sectional surface that is fixed at predetermined coordinates on the 3-D rectangular coordinate system. Therefore, the reference surface has a non-variable position on the 3-D rectangular coordinate system irrespective of translation and/or rotation of the 3-D ultrasound image.

Figure 7:
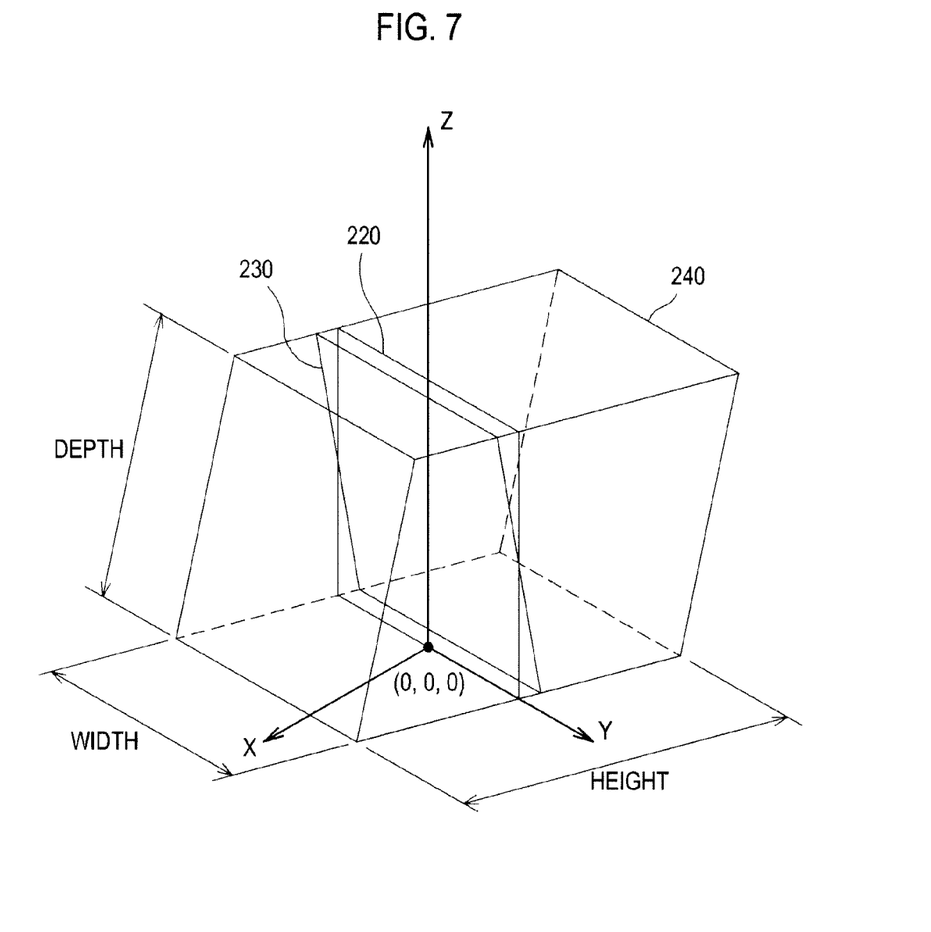
FIG. 7 is a schematic diagram illustrating an example of a 3-D rigid-body transformed ultrasound image in accordance with the present disclosure.

The similarity calculation section 145 of the processor 140 may be operable to retrieve sets of transform parameters shown in Table 1 from the storing unit 130 and then perform a rigid-body transform upon the 3-D ultrasound image 210 shown in FIG. 6 based on the retrieved sets of transform parameters to thereby form a 3-D rigid-body transformed ultrasound image 240 shown in FIG. 7, at S112. The similarity calculation section 145 may be operable to extract a reference surface image corresponding to the reference surface 220 from the 3-D rigid-body transformed ultrasound image 240, at S114. Herein, the reference surface images may be extracted from the 3-D rigid-body transformed ultrasound image 240, wherein each of the reference surface images is produced at every rigid-body transform when the sets of transform parameters are applied thereto.

Next, the similarity calculation section 145 may be operable to calculate similarities between the 2-D ultrasound image 230 and the extracted reference surface images, at S116. The similarity may be calculated through cross correlation, mutual information and the sum of squared intensity difference (SSID). In an exemplary embodiment, the similarity calculation section 145 may be operable to normalize the calculated similarities to have a value ranging from 0 to 2 by using normalized mutual information.

The similarity calculation section 145 may be operable to determine whether or not the rigid-body transform is carried out upon the 3-D ultrasound image 210 by applying all of the sets of transform parameters stored in the storing unit 130, at S118. In case all of the sets of transform parameters are not applied to the rigid-body transform, the similarity calculation section 145 may be operable to iteratively perform the above-mentioned procedures (i.e., from S112 to S116), until all of the sets of transform parameters are applied.

If all of the sets of transform parameters are applied to the rigid-body transform, the similarity calculation section 145 may then be operable to compare the respective calculated similarities with a predetermined threshold to thereby determine whether or not at least one among the calculated similarities is greater than the predetermined threshold, at S120. That is, through the above-mentioned comparison, the similarity calculation section 145 determines whether or not the 2-D ultrasound image exists in the 3-D rigid-body transformed ultrasound image.

If at least one among the calculated similarities is greater than the threshold similarity, the similarity calculation section 145 may be operable to select a maximum similarity out of the calculated similarities that are greater than the threshold similarity, at S122. In case none of the calculated similarities is greater than the threshold similarity, the similarity calculation section 145 may be operable to iteratively perform the above-mentioned procedures (i.e., from S104 to S118), until at least one calculated similarity is greater than the threshold similarity.

Next, the similarity calculation section 145 may be operable to calculate a position of the 2-D ultrasound image 230 within the 3-D rigid-body transformed ultrasound image 240 based on the set of transform parameters applied to the rigid-body transform that creates the selected maximum similarity, at S124. For example, the similarity calculation section 145 may be operable to calculate a position of the 2-D ultrasound image 230 within the 3-D rigid-body transformed ultrasound image 240 by using the set of transformation parameters (e.g., $(x_0, y_1, z_0, \theta_{x0}, \theta_{y0}, \theta_{z0})$) corresponding to the selected maximum similarity. In such case, the calculated position of the 2-dimensional ultrasound image 230 may be represented as a function of the inverse of the set of transformation parameters, e.g., $(-x_0, -y_1, -z_0, -\theta_{x0}, -\theta_{y0}, -\theta_{z0})$.

Thereafter, the CT image extraction section 146 of the processor 140 may be operable to extract a 2-D CT image corresponding to the 2-D ultrasound image the 3-D ultrasound-CT registered image based on the calculated position of the 2-dimensional ultrasound image and the relative position of the 3-D ultrasound image, at S126. Then, the display unit 150 may be operable to simultaneously display the extracted 2-D CT image and the 2-D ultrasound image, at S128. As described above, the extracted 2-D CT image and the 2-D ultrasound image may be superimposed over one another on the display unit 150, or displayed in transverse or horizontal direction.

Although exemplary embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An imaging system, comprising:
 a computerized-tomography (CT) imaging unit configured to form a 3-dimensional (3-D) CT image of a target object;
 an ultrasound image forming unit configured to form a 3-dimensional (3-D) ultrasound image of the target object and a 2-dimensional (2-D) ultrasound image of the target object;
 a storing unit configured to store sets of transform parameters for performing a rigid-body transform upon the 3-D ultrasound image;
 a processor configured to perform an image registration between the 3-D ultrasound image and the CT image to register a 3-D ultrasound-CT image, establish a 3-D coordinate system with a reference surface being set thereon in the 3-D ultrasound image, perform the rigid-body transform upon the 3-D ultrasound image by sequentially applying the sets of transformation parameters retrieved from the storing unit, calculate similarities between reference images corresponding to the reference surface and the 2-D ultrasound image, and extract a 2-D CT image corresponding to the 2-D ultrasound image from the registered 3-D ultrasound-CT image based on the calculated similarities; and
 a display unit configured to display the 2-D ultrasound image and the extracted 2-D CT image, wherein:
 each of the reference images is obtained at the rigid-body transform when the sets of transformation parameters are sequentially applied to the rigid-body transform, and
 the 2-D ultrasound image is related to a region of interest (ROI) of the target object.

2. The imaging system of claim 1, wherein the target object includes a liver.

3. The imaging system of claim 1, wherein the processor includes:
 a diaphragm extraction section configured to extract a diaphragm from the respective 3-D ultrasound and CT images of the target object by selecting a largest surface among candidate surfaces that are obtained from voxels;
 a vessel extraction section configured to extract a vessel from the respective 3-D ultrasound and CT images of the target object by selecting vessel candidates by removing voxels with a higher intensity value than a reference boundary value;
 a diaphragm refining section configured to remove clutters from the diaphragm extracted from the 3-D ultrasound image based on the extracted vessel to refine the diaphragm;

an image registration section configured to extract sample points at the diaphragm and the vessel extracted from the respective 3-D ultrasound and CT images, perform the image registration therebetween based on the extracted sample points, and calculate a relative position of the 3-D ultrasound image with respect to the 3-D CT image;

a similarity calculation section configured to establish the 3-D coordinate system and the reference surface, perform the rigid-body transform upon the 3-D ultrasound image, and calculate the similarities between the reference images and the 2-dimensional ultrasound image, to calculate a position of the 2-D ultrasound image within the 3-D ultrasound image; and a CT image extraction section configured to extract the 2-D CT image corresponding to the 2-D ultrasound image from the registered 3-D ultrasound-CT image based on the calculated relative position and the calculated position.

4. The imaging system of claim 3, wherein the diaphragm extraction section is further configured to:
obtain a flatness from voxels of the respective 3-D ultrasound and CT images with a flatness map;
select voxels having flatness greater than a reference value;
perform a morphological filtering upon the selected voxels, eliminate morphological boundaries as many as a predetermined number of the voxels, and contract and expand the morphological boundaries as many as the predetermined number of the voxels to remove the clutters, wherein voxel values exist in the morphological boundaries;
obtain the candidate surfaces from the clutter-removed voxels through an intensity-based connected component analysis (CCA); and
select the largest surface among the candidate surfaces to extract the diaphragm from the respective 3-D ultrasound and CT images.

5. The imaging system of claim 3, wherein the vessel extraction section is further configured to:
model the diaphragm to a polynomial curved surface by performing an ROI masking upon the 3-D ultrasound and CT images;
select the vessel candidates by removing voxels with the higher intensity value than the reference boundary value; and
remove non-vessel-type clutters from the selected vessel candidates to extract the vessel as a resultant vessel,
wherein the non-vessel-type clutters are removed through a structured-based vessel test, a gradient magnitude analysis and a final test.

6. The imaging system of claim 3, further comprising a user input section configured to receive input data from a user, the input data including first input data and second input data for establishing regions of the diaphragm and the vessel on the 3-D CT image, respectively.

7. The imaging system of claim 6, wherein the diaphragm extraction section is further configured to:
extract the diaphragm from the 3-D CT image in response to the first input data from the user input section;
obtain a flatness from voxels of the 3-D ultrasound image with a flatness map;
select voxels having flatness greater than a reference value;
perform a morphological filtering upon the selected voxels;
eliminate morphological boundaries as many as a predetermined number of the voxels;
contract and expand the morphological boundaries as many as the predetermined number of the voxels;
remove the clutters;
obtain candidate surfaces from the clutter-removed voxels through an intensity-based CCA; and
select the largest surface among the candidate surfaces to extract the diaphragm from the 3-D ultrasound image, wherein voxel values exist in the morphological boundaries.

8. The imaging system of claim 6, wherein the vessel extraction section is further configured to:
extract the vessel from the 3-D CT image in response to the second input data from the user input section;
extract the vessel from the 3-D ultrasound image;
model the diaphragm to a polynomial curved surface by performing an ROI masking upon the 3-D ultrasound image;
select vessel candidates by removing voxels with a higher intensity value than a reference boundary value; and
remove non-vessel-type clutters from the selected vessel candidates to extract the resultant vessel,
wherein the non-vessel-type clutters are removed through a structured-based vessel test, a gradient magnitude analysis and a final test.

9. The imaging system of claim 3, wherein the similarity calculation section is further configured to:
retrieve the sets of transformation parameters from the storing unit;
perform the rigid-body transform upon the 3-D ultrasound image by sequentially applying the retrieved sets of transformation parameters;
extract the reference surface images from the 3-D rigid-body transformed ultrasound images;
calculate the similarities between the reference surface images and the 2-D ultrasound image;
compare each of the calculated similarities with a predetermined threshold;
calculate the position of the 2-D ultrasound image based on the set of transformation parameters applied to the rigid-body transform to produce a maximum similarity among the calculated similarities, when at least one of the calculated similarities is greater than the predetermined threshold, wherein:
when none of the calculated similarities is greater than the predetermined threshold, the ultrasound image forming unit is further configured to form a new 3-D ultrasound image of the target object, and
the processor is further configured to perform the image registration between the new 3-D ultrasound image and the 3-D CT image, establish a 3-D coordinate system with a reference surface being set thereon in the new 3-D ultrasound image, perform the rigid-body transform upon the new 3-D ultrasound image by sequentially applying the sets of transformation parameters retrieved from the storing unit, calculate similarities between new reference images corresponding to the reference surface and the 2-D ultrasound image, and extract a 2-D CT image corresponding to the 2-D ultrasound image from the new 3-D ultrasound-CT registered image based on the calculated similarity.

10. The imaging system of claim 9, wherein:
the reference surface includes a cross-sectional surface fixed at predetermined coordinates on the 3-D coordinate system, and
the similarity calculation section calculates the similarities through at least one of a cross correlation, mutual information and an sum of squared intensity difference (SSID).

* * * * *